US00PP24673P2

(12) United States Plant Patent
Mak

(10) Patent No.: US PP24,673 P2
(45) Date of Patent: Jul. 22, 2014

(54) LILY PLANT NAMED 'SUNNY MARTINIQUE'

(50) Latin Name: *Lilium hybrida*
Varietal Denomination: Sunny Martinique

(75) Inventor: Niels Johannes Cornelis Mak, Wieringerwerf (NL)

(73) Assignee: Mak Breeding Rights B.V., Wieringerwerf (NL)

( * ) Notice: Subject to any disclaimer, the term of this patent is extended or adjusted under 35 U.S.C. 154(b) by 58 days.

(21) Appl. No.: 13/573,465

(22) Filed: Sep. 15, 2012

(51) Int. Cl.
*A01H 5/00* (2006.01)

(52) U.S. Cl.
USPC ..... Plt./315

(58) Field of Classification Search
CPC ..... A01H 5/0272
USPC ..... Plt./315
See application file for complete search history.

*Primary Examiner* — Annette Para
(74) *Attorney, Agent, or Firm* — C. A. Whealy

(57) ABSTRACT

A new and distinct cultivar of Lily plant named 'Sunny Martinique', characterized by its compact and upright plant habit; vigorous growth habit; strong leaves that do not yellow with cool temperatures; freely flowering habit; upright flower buds; dark pink-colored flowers with white-colored margins; and good postproduction longevity.

1 Drawing Sheet

Botanical designation: *Lilium hybrida.*
Cultivar denomination: 'SUNNY MARTINIQUE'.

BACKGROUND OF THE INVENTION

The present Invention relates to a new and distinct cultivar of Lily plant, commercially known as Oriental Hybrid Lily, botanically known as *Lilium hybrida* and hereinafter referred to by the name 'Sunny Martinique'.

The new Oriental Hybrid Lily plant is a product of a planned breeding program conducted by the Inventor in Wieringerwerf, The Netherlands. The objective of the breeding program is to develop new compact potted Oriental Hybrid Lily plants with strong leaves, large attractive flowers and good postproduction longevity.

The new Oriental Hybrid Lily plant originated from a cross-pollination in 2001 of two unnamed proprietary seedling selections of *Lilium hybrida*, not patented. The new Oriental Hybrid Lily plant was discovered and selected by the Inventor as a single flowering plant from within the resultant progeny of the stated cross-pollination in a controlled greenhouse environment in Wieringerwerf, The Netherlands in May, 2005.

Asexual reproduction of the new Oriental Hybrid Lily plant by bulb scales in a controlled greenhouse environment in Wieringerwerf, The Netherlands since November, 2005 has shown that the unique features of this new Oriental Hybrid Lily plant are stable and reproduced true to type in successive generations.

SUMMARY OF THE INVENTION

Plants of the new Oriental Hybrid Lily have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunny Martinique'. These characteristics in combination distinguish 'Sunny Martinique' as a new and distinct Oriental Hybrid Lily plant:

1. Compact and upright plant habit.
2. Vigorous growth habit.
3. Strong leaves that do not yellow with cool temperatures.
4. Freely flowering habit.
5. Upright flower buds.
6. Dark pink-colored flowers with white-colored margins.
7. Good postproduction longevity.

Plants of the new Oriental Hybrid Lily differ primarily from plants of the female parent selection in the following characteristics:

1. Plants of the new Oriental Hybrid Lily are taller than plants of the female parent selection.
2. Plants of the new Oriental Hybrid Lily have larger flowers than plants of the female parent selection.
3. Plants of the new Oriental Hybrid Lily and the female parent selection differ in flower color as plants of the female parent selection have reddish pink-colored flowers.

Plants of the new Oriental Hybrid Lily differ primarily from plants of the male parent selection in the following characteristics:

1. Plants of the new Oriental Hybrid Lily are more compact than plants of the male parent selection.
2. Plants of the new Oriental Hybrid Lily and the male parent selection differ in flower color as plants of the male parent selection have pink-colored flowers.

Plants of the new Oriental Hybrid Lily can be compared to plants of Oriental Hybrid Lily 'After Eight', not patented. Plants of the new Oriental Hybrid Lily differ from plants of 'After Eight' in the following characteristics:

1. Leaves of plants of the new Oriental Hybrid Lily are strong and do not yellow with cool temperatures whereas leaves of plants of 'After Eight' are not as strong and yellow with cool temperatures.

2. Flowers of plants of the new Oriental Hybrid Lily are lighter pink in color than flowers of plants of 'After Eight'.

DESCRIPTION OF THE PHOTOGRAPH

The accompanying colored photograph illustrates the overall appearance of the new Oriental Hybrid Lily plant showing the colors as true as it is reasonably possible to obtain in colored reproductions of this type. Colors in the photograph may differ slightly from the color values cited in the detailed botanical description which accurately describe the colors of the new Oriental Hybrid Lily plant. The photograph comprises a side perspective view of a typical flowering plant of 'Sunny Martinique' grown in a container.

DETAILED BOTANICAL DESCRIPTION

The aforementioned photograph and following observations and measurements describe plants grown during the spring in 15-cm containers in a glass-covered greenhouse in Wieringerwerf, The Netherlands and under cultural conditions typically used in Oriental Hybrid Lily commercial production. During the production of the plants, day temperatures averaged 18° C., night temperatures averaged 15° C. and light levels averaged 6,000 lux. Measurements and numerical values represent averages for typical flowering plants. Plants were 110 days old when the photograph and description were taken. In the following description, color references are made to The Royal Horticultural Society Colour Chart, 2007 Edition, except where general terms of ordinary dictionary significance are used.

Botanical classification: *Lilium hybrida* 'Sunny Martinique'.

Parentage:

*Female, or seed, parent*.—Unnamed proprietary seedling selection of *Lilium hybrida*, not patented.

*Male, or pollen, parent*.—Unnamed proprietary seedling selection of *Lilium hybrida*, not patented.

Plant description:

*Plant form and growth habit*.—Upright flowering plant; single erect flowering stem with a terminal cluster of flowers; compact and dense plant habit; vigorous growth habit.

*Plant height, soil level to top of flowers*.—About 46 cm.

*Plant diameter or spread*.—About 21 cm.

*Plant circumference*.—About 66 cm.

*Bulbs*.—Diameter: About 10 cm to 20 cm. Texture: Smooth. Color: Close to 155D.

*Flowering stems*.—Diameter: About 9 mm. Internode length: Towards the base, about 5 cm; towards the apex, about 3 cm. Strength: Strong. Texture: Smooth, glabrous. Color: Towards the base, close to 189A; towards the apex, close to 138B.

*Leaves*.—Arrangement and quantity: Alternate; simple; sessile; about 31 leaves develop per plant; leaves roughly horizontal. Length, upper leaves: About 15 cm. Width, upper leaves: About 7.5 cm. Length, lower leaves: About 11 cm. Width, lower leaves: About 3.5 cm. Shape: Lanceolate. Apex: Acute. Base: Acutely cuneate. Margin: Entire. Texture, upper and lower surfaces: Glabrous, smooth; leathery. Venation pattern: Parallel. Color: Developing and fully expanded leaves, upper surface: Close to 137A; venation, close to 137A. Developing and fully expanded leaves, lower surface: Close to 137C; venation, close to 137C.

Flower description:

*Flower shape and aspect*.—Flowers umbellate and funnel-shaped; when fully opened, flowers flatten and tepals recurve towards the apex; flower buds face upright and flowers face upright to outwardly.

*Flowering habit*.—Freely flowering habit, large bulbs will produce five to nine flowers per flowering stem.

*Fragrance*.—Slightly fragrant; pleasant.

*Natural flowering season*.—Plants flower in June and July in The Netherlands; plants can be flowered year-round in the greenhouse and forced to bloom about 100 days after planting bulbs.

*Postproduction longevity*.—Good postproduction longevity, flowers last about 15 days on the plant; tepals not persistent; gynoecium persistent.

*Flower buds*.—Length: About 13 cm. Diameter: About 4.5 cm. Circumference: About 13 cm. Shape: Lanceolate. Color: Close to 144C; color becoming closer to 70C with development; sutures, close to 144C.

*Flower size*.—Diameter: About 20 cm. Length (height): About 8 cm.

*Perianth*.—Quantity and arrangement: Six tepals per flower arranged in two whorls; tepals imbricate. Tepal length, inner tepals: About 13.5 cm. Tepal width, inner tepals: About 7.5 cm. Tepal length, outer tepals: About 14 cm. Tepal width, outer tepals: About 5 cm. Tepal shape: Lanceolate. Tepal apex: Acute. Tepal margin: Entire; slightly undulate. Tepal texture, upper and lower surfaces: Smooth, glabrous. Tepal color: When opening and fully opened, upper surface: Close to 60A; margins, close to 155D; towards the base, close to 12A and at the base, close to 149A; spots, close to 185A; color becoming closer to 59A and 64A with development. When opening and fully opened, lower surface: Close to 64D; color becoming closer to 75B with development.

*Pedicels*.—Length: About 4 cm. Diameter: About 5 mm. Angle: About 45° to 70° from vertical. Strength: Strong. Texture: Smooth, glabrous. Color: Close to 137C.

*Reproductive organs*.—Stamens: Quantity per flower: Six. Filament length: About 8 cm. Filament color: Between 155D and 145A. Anther length: About 1.6 cm. Anther color: Close to 183D. Pollen color: Close to 169B. Pistils: Quantity per flower: One. Style length: About 7.6 cm. Style color: Close to 144D to 144A. Stigma diameter: About 7 mm. Stigma shape: Lobed. Stigma color: Close to 186C.

*Fruits*.—Length: About 2.4 cm. Diameter: About 5 mm. Color: Close to 144C.

*Seeds*.—No viable seeds have been observed on plants of the new Oriental Hybrid Lily plant.

Disease & pest resistance: Resistance to pathogens and pests common to Oriental Hybrid Lilies has not been observed on plants of the new Oriental Hybrid Lily.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Sunny Martinique' as illustrated and described.

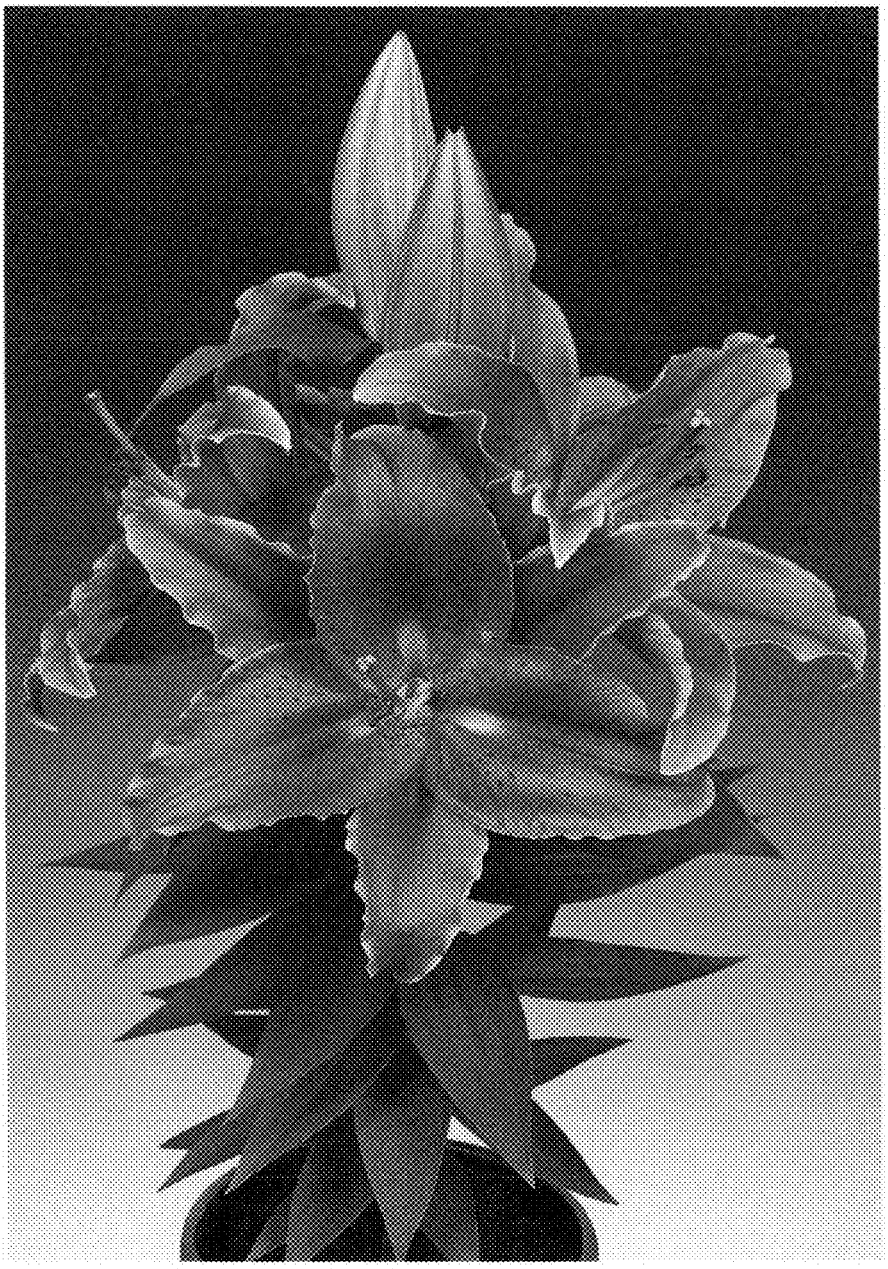

* * * * *